US012655103B2

(12) United States Patent
Liu et al.

(10) Patent No.: US 12,655,103 B2
(45) Date of Patent: Jun. 16, 2026

(54) **METHODS FOR PREPARING *L*-6-HYDROXYTRYPTOPHAN (HTP) DERIVATIVE AND INTERMEDIATES THEREOF**

(71) Applicants: INNER MONGOLIA UNIVERSITY, Huhhot (CN); INNER MONGOLIA DUHE INNOVATION R & D TECH CO., LTD, Huhhot (CN)

(72) Inventors: Guodu Liu, Huhhot (CN); Xinlong Yan, Huhhot (CN); Zongwei Li, Huhhot (CN)

(73) Assignee: INNER MONGOLIA UNIVERSITY, Huhhot (CN)

( * ) Notice: Subject to any disclaimer, the term of this patent is extended or adjusted under 35 U.S.C. 154(b) by 3 days.

(21) Appl. No.: 18/994,183

(22) PCT Filed: Jun. 4, 2024

(86) PCT No.: PCT/CN2024/097148
§ 371 (c)(1),
(2) Date: Jan. 14, 2025

(87) PCT Pub. No.: WO2024/188373
PCT Pub. Date: Sep. 19, 2024

(65) Prior Publication Data

US 2026/0001842 A1 Jan. 1, 2026

(30) Foreign Application Priority Data

Mar. 7, 2024 (CN) ......................... 202410256775.9

(51) Int. Cl.
*C07D 209/20* (2006.01)
*C07F 7/10* (2006.01)

(52) U.S. Cl.
CPC .................................. *C07D 209/20* (2013.01)

(58) Field of Classification Search
CPC ................................ C07D 209/20; C07F 7/10
See application file for complete search history.

(56) References Cited

U.S. PATENT DOCUMENTS 3,808,101 A 4/1974 Ajinomoto

FOREIGN PATENT DOCUMENTS

CN 115715294 A 2/2023
CN 116606236 A 8/2023
CN 117843672 A 4/2024

OTHER PUBLICATIONS

Matinkhoo, K., A.. Pryyma, M. Todorovic, B. Patrick, and D. Perrin, "Synthesis of the Death-Cap Mushroom Toxin α-Amanitin", J. Am. Chem. Soc. (2018), 140, pp. 6513-6517. (Year: 2018).*

Supplemental information of Matinkhoo, K., A.. Pryyma, M. Todorovic, B. Patrick, and D. Perrin, "Synthesis of the Death-Cap Mushroom Toxin α-Amanitin", J. Am. Chem. Soc. (2018), 140, pp. 6513-6517. (Year: 2018).*

Feng et al: "Total Synthesis of Verruculogen and Fumitremorgin A Enabled by Ligand-Controlled C—H Borylation", Journal of the American Chemical Society, vol. 137, p. 10160-10163, Aug. 9, 2015.

Matinkhoo et al: "Synthesis of the Death-Cap Mushroom Toxin [alpha]-Amanitin", Journal of the American Chemical Society, vol. 140, p. 6513-6517, Mar. 21, 2018.

Matinkhoo et al: "Supporting Information: Synthesis of the Death-Cap Mushroom Toxin [alpha]-Amanitin", Journal of the American Chemical Society, vol. 140, Mar. 21, 2018.

Yao et al: "Iodine-Mediated Tryptathionine Formation Facilitates the Synthesis of Amanitins", Journal of the American Chemical Society, vol. 143, p. 14322-14331, Aug. 30, 2021.

* cited by examiner

*Primary Examiner* — Kamal A Saeed
*Assistant Examiner* — Sagar Patel
(74) *Attorney, Agent, or Firm* — WCF IP

(57) ABSTRACT

Methods for preparing an L-6-hydroxytryptophan (HTP) derivative and intermediates thereof are provided. The methods for preparing the various intermediates of the L-6-HTP derivative are provided, on the basis of which the L-6-HTP derivative could be obtained. Specifically, the L-6-HTP derivative is obtained by using a compound A6-0 with a structure shown in Formula 1 as a starting reaction raw material, and subjecting the compound A6-0 to triisopropylsilyl (TIPS) protection, coupling, carbon-boron bond oxidation, hydroxyl-targeted benzyl protection, TIPS protective group removal, tert-butoxycarbonyl (Boc) protective group removal, methyl ester hydrolysis, and amino-targeted 9-fluorenylmethoxycarbonyl (Fmoc) protection in sequence.

Formula 1

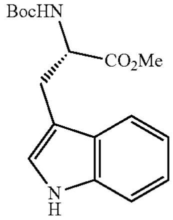

11 Claims, No Drawings

METHODS FOR PREPARING *L*-6-HYDROXYTRYPTOPHAN (HTP) DERIVATIVE AND INTERMEDIATES THEREOF

CROSS-REFERENCE TO RELATED APPLICATION

The present application is a national stage application of International Patent Application No. PCT/CN2024/097148, filed on Jun. 4, 2024, which claims priority to the Chinese Patent Application No. CN202410256775.9, entitled "METHODS FOR PREPARING L-6-HYDROXYTRYPTOPHAN (HTP) DERIVATIVE AND INTERMEDIATES THEREOF" filed with the China National Intellectual Property Administration (CNIPA) on Mar. 7, 2024. The disclosure of the two applications is incorporated herein by reference in its entirety.

TECHNICAL FIELD

The present disclosure relates to the technical field of pharmaceutical intermediate synthesis, and in particular to methods for preparing an L-6-hydroxytryptophan (HTP) derivative and intermediates thereof.

BACKGROUND

Tryptophan, also known as amino-indolepropionic acid, has isomers including L-type, D-type and DL-type, of which only the L-type could be absorbed by human body. As one of the essential amino acids, the tryptophan has a great influence on the growth, development, and metabolism of humans and animals. The human body and animals are prone to lack of L-tryptophan, and could not synthesize the same by themselves and must obtain the same from food. Therefore, there is an extremely high potential demand for the L-tryptophan. The L-tryptophan is currently widely used in medicine, food, and feed. Currently, technologies for the production of the L-tryptophan and derivatives thereof have become increasingly mature after years of research and development. For example, the L-tryptophan and derivatives thereof could be prepared through protein hydrolysis or microbial fermentation.

However, technologies for the production of L-hydroxytryptophan (HTP) and derivatives thereof still need to be further developed. L-5-hydroxytryptophan (L-5-HTP) is a natural amino acid as well as a dietary supplement that acts as an antidepressant, appetite suppressant, or sleep aid. The L-5-HTP is also a precursor to the neurotransmitter serotonin and an antagonist of reserpine. L-6-hydroxytryptophan (L-6-HTP), as a building block for a key non-natural chiral amino acid of amanitin-type cyclic peptide toxin compounds, shows important applications in the efficient total synthesis of payloads for such cyclic peptide toxin compounds. The L-6-HTP exhibits huge potential demand in the peptide medicine, food, and feed industries. So far, there is no microbial fermentation route for the preparation of the L-6-HTP and its derivatives. The chemical synthesis methods in the prior art all face the problems of cumbersome routes, high production costs, and low product yields.

SUMMARY

An object of the present disclosure is to provide methods for preparing an L-6-HTP derivative and intermediates thereof. In the present disclosure, the method has the advantages of short process flow, convenient operations, low production cost, and high product yield in preparing the L-6-HTP derivative and intermediates thereof.

To achieve the above object, the present disclosure provides the following technical solutions.

The present disclosure provides a method for preparing an intermediate C of an L-6-HTP derivative, including the following steps:

- subjecting a compound A6-0 to triisopropylsilyl (TIPS) protection to obtain an intermediate A of the L-6-HTP derivative;
- subjecting the intermediate A of the L-6-HTP derivative to coupling to obtain an intermediate B of the L-6-HTP derivative; and
- subjecting the intermediate B of the L-6-HTP derivative to carbon-boron bond oxidation to obtain the intermediate C of the L-6-HTP derivative; where
- the compound A6-0, the intermediate A of the L-6-HTP derivative, the intermediate B of the L-6-HTP derivative, and the intermediate C of the L-6-HTP derivative have structures shown in Formula 1, Formula 2, Formula 3, and Formula 4, respectively:

Formula 1

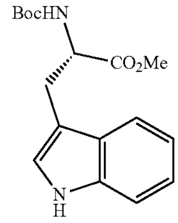

;

Formula 2

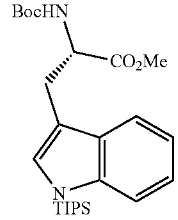

;

Formula 3

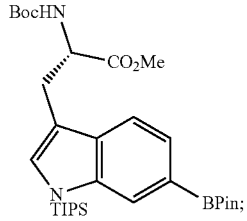

;

Formula 4

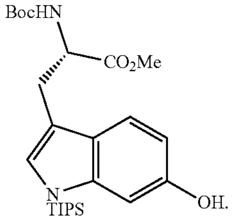

.

The present disclosure further provides a method for preparing an intermediate D of an L-6-HTP derivative, including the following steps:

- preparing the intermediate C of the L-6-HTP derivative by the method described in the above technical solution; and subjecting the intermediate C of the L-6-HTP derivative to hydroxyl-targeted benzyl protection to obtain the intermediate D of the L-6-HTP derivative;

where the intermediate D of the L-6-HTP derivative has a structure shown in Formula 5:

Formula 5

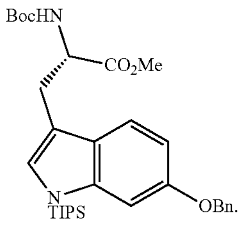

The present disclosure further provides a method for preparing an intermediate E of an L-6-HTP derivative, including the following steps:

preparing the intermediate D of the L-6-HTP derivative by the method described in the above technical solution; and subjecting the intermediate D of the L-6-HTP derivative to TIPS protective group removal to obtain the intermediate E of the L-6-HTP derivative;

where the intermediate E of the L-6-HTP derivative has a structure shown in Formula 6:

Formula 6

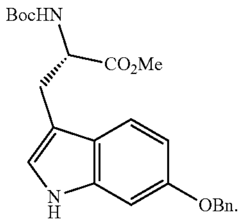

The present disclosure further provides a method for preparing an intermediate F of an L-6-HTP derivative, including the following steps:

preparing the intermediate E of the L-6-HTP derivative by the method described in the above technical solution; and subjecting the intermediate E of the L-6-HTP derivative to tert-butoxycarbonyl (Boc) protective group removal to obtain the intermediate F of the L-6-HTP derivative;

where the intermediate F of the L-6-HTP derivative has a structure shown in Formula 7:

Formula 7

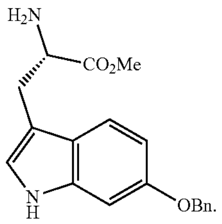

The present disclosure further provides a method for preparing an L-6-HTP derivative, including the following steps:

preparing the intermediate F of the L-6-HTP derivative by the method described in the above technical solution; and subjecting the intermediate F of the L-6-HTP derivative to methyl ester hydrolysis and amino-targeted 9-fluorenylmethoxycarbonyl (Fmoc) protection to obtain the L-6-HTP derivative;

where the L-6-HTP derivative has a structure shown in Formula 8:

Formula 8

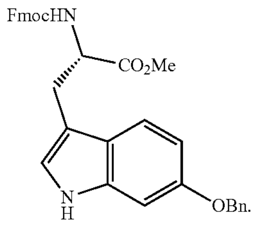

In some embodiments, a raw material for the TIPS protection is triisopropylsilyl chloride (TIPSCl), and a molar ratio of the TIPSCl to the compound A6-0 is in a range of 0.15-0.2:0.15; and the TIPS protection is conducted in the presence of lithium bis(trimethylsilyl)amide (LiHMDS) and an organic solvent, and a dosage ratio of the LiHMDS, the organic solvent, and the compound A6-0 is in a range of 0.15-0.20 mol:0.3-1 L:0.15 mol.

In some embodiments, the TIPS protection is conducted at a temperature of 0° C. to 50° C. for 0.1 h to 2 h.

In some embodiments, where after the TIPS protection is completed, the method further includes: adding a saturated $NH_4Cl$ solution into a resulting protection reaction system to quench the TIPS protection, conducting extraction, removing the organic solvent from a resulting organic phase, and subjecting a resulting crude product to separation by column chromatography to obtain the intermediate A of the L-6-HTP derivative.

In some embodiments, raw materials for the coupling include pinacolborane and bis(pinacolato)diboron, and a molar ratio of the intermediate A of the L-6-HTP derivative, the pinacolborane, and the bis(pinacolato)diboron is in a range of 1:0.2-0.3:3.5-4.5; and the coupling is conducted in the presence of (1,5-cyclooctadiene)(methoxy)iridium(I) dimer ($[Ir(cod)(OMe)]_2$), 1,10-phenanthroline (phen), and an organic solvent, and a dosage ratio of the intermediate A of the L-6-HTP derivative, the (1,5-cyclooctadiene)(methoxy)iridium (I) dimer, the 1,10-phenanthroline, and the organic solvent is in a range of 1 mol:0.04-0.06 mol:0.08-0.12 mol:3-7 L.

In some embodiments, the coupling is conducted at a temperature of 70° C. to 90° C. for 1 h to 24 h.

In some embodiments, after the coupling is completed, the method further includes: adding a saturated $NaHCO_3$ solution into a resulting coupling reaction system to quench the coupling, conducting extraction, removing the organic solvent from a resulting organic phase, and subjecting a resulting crude product to separation by column chromatography to obtain the intermediate B of the L-6-HTP derivative.

In some embodiments, the carbon-boron bond oxidation is conducted in the presence of sodium perborate tetrahydrate and potassium tert-butoxide (KTB).

In some embodiments, a molar ratio of the intermediate B of the L-6-HTP derivative, the sodium perborate tetrahydrate, and the KTB is in a range of 1: 2-10:1-5; and the carbon-boron bond oxidation is conducted in the presence of an organic solvent and water, and a dosage ratio of the organic solvent, the water, and the intermediate B of the L-6-HTP derivative is in a range of 0.5-3 L:0.5-3 L:0.1 mol.

In some embodiments, the carbon-boron bond oxidation includes a first-stage reaction and a second-stage reaction in sequence; the first-stage reaction is conducted at a temperature of −10° C. to 10° C. for 1 h to 2 h; and the second-stage reaction is conducted at a temperature of 0° C. to 25° C. for 1 h to 24 h.

In some embodiments, after the carbon-boron bond oxidation is completed, the method further includes: subjecting a resulting product to extraction, removing the organic solvent from a resulting organic phase, and subjecting a resulting crude product to separation by column chromatography to obtain the intermediate C of the L-6-HTP derivative.

In some embodiments, a benzyl reagent for the hydroxyl-targeted benzyl protection includes benzyl bromide, and the hydroxyl-targeted benzyl protection is conducted in the presence of potassium iodide and potassium carbonate.

In some embodiments, a molar ratio of the intermediate C of the L-6-HTP derivative, the benzyl bromide, the potassium iodide, and the potassium carbonate is in a range of 1:1-5:0.05-1:1-5; and the hydroxy-targeted benzyl protection is conducted in the presence of an organic solvent, and a dosage ratio of the organic solvent to the intermediate C of the L-6-HTP derivative is in a range of 0.5-2 L:0.1 mol.

In some embodiments, the hydroxy-targeted benzyl protection is conducted at a temperature of 30° C. to 100° C. for 2 h to 24 h.

In some embodiments, after the hydroxy-targeted benzyl protection is completed, the method further includes: subjecting a resulting product to extraction, removing the organic solvent from a resulting organic phase, and subjecting a resulting crude product to separation by column chromatography to obtain the intermediate D of the L-6-HTP derivative.

In some embodiments, the TIPS protective group removal is conducted in the presence of tetrabutylammonium fluoride (TBAF).

In some embodiments, a molar ratio of the intermediate D of the L-6-HTP derivative to the TBAF is in a range of 1:1-5; and the TIPS protective group removal is conducted in the presence of an organic solvent, and a dosage ratio of the organic solvent to the intermediate D of the L-6-HTP derivative is in a range of 0.5-2 L:1 mol.

In some embodiments, the TIPS protective group removal is conducted at a temperature of 0° C. to 50° C. for 0.2 h to 6 h.

In some embodiments, after the TIPS protective group removal is completed, the method further includes: subjecting a resulting product to extraction, removing the organic solvent from a resulting organic phase, and subjecting a resulting crude product to separation by column chromatography to obtain the intermediate E of the L-6-HTP derivative.

In some embodiments, the Boc protective group removal is conducted in the presence of trifluoroacetic acid (TFA).

In some embodiments, a dosage ratio of the TFA to the intermediate E of the L-6-HTP derivative is in a range of 0.5-3 L:0.1 mol; and the Boc protective group removal is conducted in the presence of an organic solvent, and a volume ratio of the organic solvent to the TFA is in a range of 1-6:3.

In some embodiments, the Boc protective group removal is conducted at a temperature of 0° C. to 50° C. for 0.2 h to 6 h.

In some embodiments, after the Boc protective group removal is completed, the method further includes: removing the organic solvent from a resulting product, and subjecting a resulting crude product to separation by column chromatography to obtain the intermediate F of the L-6-HTP derivative.

In some embodiments, the methyl ester hydrolysis is conducted in the presence of sodium hydroxide, an organic solvent, and water; a molar ratio of the intermediate F of the L-6-HTP derivative to the sodium hydroxide is in a range of 1:1-10; and a dosage ratio of the organic solvent, the water, and the intermediate F of the L-6-HTP derivative is in a range of 0.5-3 L:0.5-2 L:1 mol.

In some embodiments, the methyl ester hydrolysis is conducted at a temperature of 0° C. to 50° C. for 0.5 h to 6 h.

In some embodiments, a raw material for the amino-targeted Fmoc protection includes 9-fluorenylmethoxycarbonyl chloride (Fmoc-Cl), and the amino-targeted Fmoc protection is conducted in the presence of sodium carbonate, an organic solvent, and water; based on a dosage of the intermediate F of the L-6-HTP derivative, a molar ratio of the intermediate F of the L-6-HTP derivative, the Fmoc-Cl, and the sodium carbonate is in a range of 1:1-3:1-3; and a dosage ratio of the organic solvent, the water, and the intermediate F of the L-6-HTP derivative is in a range of 0.5-3 L:0.5-2 L:1 mol.

In some embodiments, the amino-targeted Fmoc protection is conducted at a temperature of 0° C. to 50° C. for 1 h to 24 h.

In some embodiments, after the amino-targeted Fmoc protection is completed, the method further includes: subjecting a resulting product to extraction, removing the organic solvent from a resulting organic phase, and subjecting a resulting crude product to separation by column chromatography to obtain the L-6-HTP derivative.

The present disclosure further provides an intermediate for synthesizing an L-6-HTP derivative, including a compound having a structure shown in Formula 4, Formula 5, or Formula 6:

Formula 4

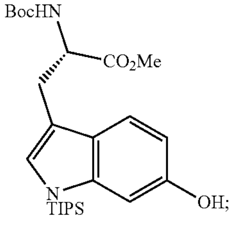

-continued

Formula 5

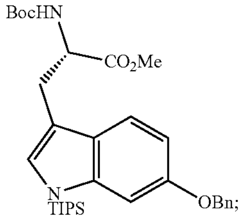

Formula 6

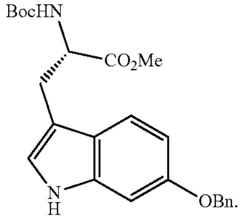

Beneficial Technical Effects

In the present disclosure, methods for preparing the various intermediates of the L-6-HTP derivative are provided, and on the basis of this, the L-6-HTP derivative could be obtained, with a high product yield and a low production cost. Specifically, a compound A6-0 with a structure shown in Formula 1 is used as a starting reaction raw material. The starting reaction raw material is easy to purchase through commercial channels and inexpensive. The compound A6-0 is subjected to TIPS protection to obtain an intermediate A of the L-6-HTP derivative having a structure shown in Formula 2. The intermediate A of the L-6-HTP derivative is subjected to coupling to obtain an intermediate B of the L-6-HTP derivative having a structure shown in Formula 3. The intermediate B of the L-6-HTP derivative is subjected to carbon-boron bond oxidation to obtain an intermediate C of the L-6-HTP derivative having the structure shown in Formula 4. The intermediate C of the L-6-HTP derivative is subjected to hydroxyl-targeted benzyl protection to obtain an intermediate D of the L-6-HTP derivative having the structure shown in Formula 5. The intermediate D of the L-6-HTP derivative is subjected to TIPS protective group removal to obtain an intermediate E of the L-6-HTP derivative having the structure shown in Formula 6. The intermediate E of the L-6-HTP derivative is subjected to Boc protective group removal to obtain an intermediate F of the L-6-HTP derivative having the structure shown in Formula 7. The intermediate F of the L-6-HTP derivative is subjected to methyl ester hydrolysis and amino-targeted Fmoc protection to obtain an L-6-HTP derivative having the structure shown in Formula 8. The methods result in a high product yield, have a short process flow, and are easy for operation, thereby realizing the large-scale production.

Furthermore, the methods show mild reaction conditions, high selectivity, and desirable operability of the separation and purification, which are convenient for further synthesis of polypeptides and bioactive small molecules.

DETAILED DESCRIPTION OF THE EMBODIMENTS

The present disclosure provides a method for preparing an intermediate C of an L-6-HTP derivative, including the following steps:

subjecting a compound A6-0 to triisopropylsilyl (TIPS) protection to obtain an intermediate A of the L-6-HTP derivative;

subjecting the intermediate A of the L-6-HTP derivative to coupling to obtain an intermediate B of the L-6-HTP derivative; and subjecting the intermediate B of the L-6-HTP derivative to carbon-boron bond oxidation to obtain the intermediate C of the L-6-HTP derivative; where the compound A6-0, the intermediate A of the L-6-HTP derivative, the intermediate B of the L-6-HTP derivative, and the intermediate C of the L-6-HTP derivative have structures shown in Formula 1, Formula 2, Formula 3, and Formula 4, respectively:

Formula 1

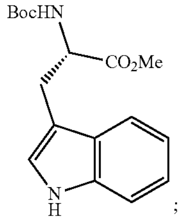

Formula 2

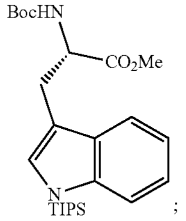

Formula 3

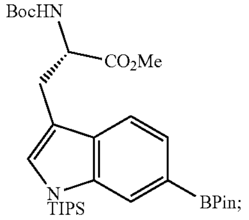

Formula 4

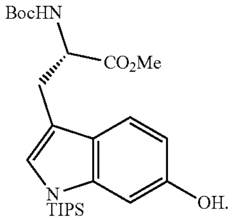

In the present disclosure, unless otherwise specified, all raw materials used are commercially available products well known to those skilled in the art.

In the present disclosure, a compound A6-0 is subjected to TIPS protection to obtain an intermediate A of the L-6-HTP derivative. In some embodiments of the present disclosure, a raw material for the TIPS protection is TIPSCl. In some embodiments of the present disclosure, a molar ratio of the TIPSCl to the compound A6-0 is in a range of 0.15-0.2:0.15, and preferably 0.18:0.15. In some embodiments of the present disclosure, the TIPS protection is conducted in the presence of LiHMDS and an organic solvent. In some embodiments of the present disclosure, the organic solvent is tetrahydrofuran (THF). In some embodiments of the present disclosure, a dosage ratio of the LiHMDS, the organic solvent, and the compound A6-0 is in a range of 0.15-0.20 mol:0.3-1 L:0.15 mol, and preferably 0.18 mol:0.48 L:0.15 mol.

In some embodiments of the present disclosure, the compound A6-0 is mixed with the THF, then a solution of the LiHMDS in THF is added into a resulting mixture; a resulting mixed solution is subjected to pre-reaction, then a solution of the TIPSCl in THF is added into a resulting resection system; and a resulting mixture is subjected to the TIPS protection. In some embodiments of the present disclosure, the pre-reaction is conducted at a temperature of −70° C. to −85° C., and preferably −78° C. In some embodiments of the present disclosure, the pre-reaction is conducted for 0.1 h to 2 h, and preferably 1 h. In some embodiments of the present disclosure, the TIPS protection is conducted at a temperature of 0° C. to 50° C., and preferably room temperature. In some embodiments of the present disclosure, the TIPS protection is conducted for 0.1 h to 2 h, and preferably 1 h. In some embodiments of the present disclosure, the pre-reaction and TIPS protection each are conducted under nitrogen protection.

In some embodiments of the present disclosure, the method further includes the following steps after the TIPS protection is completed: adding a saturated $NH_4Cl$ solution into a resulting reaction system to quench the TIPS protection, conducting extraction, removing the organic solvent from a resulting organic phase, and subjecting a resulting crude product to separation by column chromatography to obtain the intermediate A of the L-6-HTP derivative. In some embodiments of the present disclosure, an organic reagent used in the extraction is ethyl acetate. In some embodiments of the present disclosure, after the extraction, drying is conducted, and a desiccant used in the drying is anhydrous sodium sulfate. In some embodiments of the present disclosure, after the drying, filtration is conducted to remove the organic solvent in a filtrate to obtain the crude product. In some embodiments of the present disclosure, removing the organic solvent is performed by vacuum distillation, and the organic solvent can be recycled. In some embodiments of the present disclosure, a silica gel for the separation is 200-300 mesh silica gel. In some embodiments of the present disclosure, an eluent for the separation is a mixture of petroleum ether and ethyl acetate. In some embodiments of the present disclosure, a volume ratio of the petroleum ether to the ethyl acetate is in a range of 95:5.

In the present disclosure, after the intermediate A of the L-6-HTP derivative is obtained, the intermediate A of the L-6-HTP derivative is subjected to coupling to obtain an intermediate B of the L-6-HTP derivative. In some embodiments of the present disclosure, raw materials for the coupling include pinacolborane and bis(pinacolato)diboron. In some embodiments of the present disclosure, a molar ratio of the intermediate A of the L-6-HTP derivative, the pinacolborane, and the bis(pinacolato)diboron is in a range of 1:0.2-0.3:3.5-4.5, and preferably 1:0.25:4. In some embodiments of the present disclosure, the coupling is conducted in the presence of (1,5-cyclooctadiene)(methoxy)iridium(I) dimer ($[Ir(cod)(OMe)]_2$), 1,10-phenanthroline (phen), and an organic solvent. In some embodiments of the present disclosure, the organic solvent is n-hexane. In some embodiments of the present disclosure, a dosage ratio of the intermediate A of the L-6-HTP derivative, the (1,5-cyclooctadiene)(methoxy)iridium(I) dimer, the 1,10-phenanthroline, and the organic solvent is in a range of 1 mol:0.04-0.06 mol:0.08-0.12 mol:3-7 L, and preferably 1 mol:0.05 mol:0.1 mol:6 L.

In some embodiments of the present disclosure, the (1,5-cyclooctadiene)(methoxy)iridium(I) dimer, the 1,10-phenanthroline, and a part of the organic solvent are mixed to obtain a mixed solution, the mixed solution is subjected to complexation; then the pinacolborane, the intermediate A of the L-6-HTP derivative, and the bis(pinacolato)diboron are added to a resulting system to obtain a mixture, and the mixture is subjected to the coupling. In some embodiments of the present disclosure, the complexation is conducted at a temperature of 0° C. to 50° C., and preferably room temperature. In an example of the present disclosure, the room temperature is specifically 25° C. In some embodiments of the present disclosure, the complexation is conducted for 2 min to 15 min, and preferably 10 min. In some embodiments of the present disclosure, the coupling is conducted at a temperature of 70° C. to 90° C., and preferably 80° C. In some embodiments of the present disclosure, the coupling is conducted for 1 h to 24 h, and preferably 12 h to 24 h.

In the present disclosure, the method further includes the following steps after the coupling is completed: adding a saturated $NaHCO_3$ solution into a resulting reaction system to quench the coupling, conducting extraction, removing the organic solvent from a resulting organic phase, and subjecting a resulting crude product to separation by column chromatography to obtain the intermediate B of the L-6-HTP derivative. In some embodiments of the present disclosure, an organic reagent used in the extraction is ethyl acetate. In some embodiments of the present disclosure, after the extraction, drying is conducted, and a desiccant used in the drying is anhydrous sodium sulfate. In some embodiments of the present disclosure, after the drying, filtration is conducted to remove the organic solvent in a filtrate to obtain the crude product. In some embodiments of the present disclosure, a process for removing the organic solvent is vacuum distillation, and the organic solvent can be recycled. In some embodiments of the present disclosure, a silica gel for the separation is 200-300 mesh silica gel. In some embodiments of the present disclosure, an eluent for the separation is a mixture of petroleum ether and ethyl acetate. In some embodiments of the present disclosure, a volume ratio of the petroleum ether to the ethyl acetate is in a range of 95:5.

In the present disclosure, after the intermediate B of the L-6-HTP derivative is obtained, the intermediate B of the L-6-HTP derivative is subjected to carbon-boron bond oxidation to obtain an intermediate C of the L-6-HTP derivative. In some embodiments of the present disclosure, the carbon-boron bond oxidation is conducted in the presence of sodium perborate tetrahydrate and KTB. In some embodiments of the present disclosure, a molar ratio of the intermediate B of the L-6-HTP derivative, the sodium perborate tetrahydrate, and the KTB is in a range of 1: 2-10:1-5, and preferably 1:1.5:1.1. In some embodiments of the present disclosure, the carbon-boron bond oxidation is conducted in the presence of an organic solvent and water. In some embodiments of the present disclosure, the organic solvent is one or more selected from the group consisting of THF, methanol, and dioxane, and preferably the THF. In some embodiments of the present disclosure, a dosage ratio of the organic solvent, the water, and the intermediate B of the L-6-HTP derivative is in a range of 0.5-3 L:0.5-3 L:0.1 mol, and preferably 1-3 L:1-3 L:0.1 mol.

In some embodiments of the present disclosure, the intermediate B of the L-6-HTP derivative is dissolved in the organic solvent, then the KTB, the sodium perborate tetrahydrate, and the water are added in sequence, and a resulting system is subjected to the carbon-boron bond oxidation. In some embodiments of the present disclosure, the carbon-boron bond oxidation includes a first-stage reaction and a second-stage reaction in sequence. In some embodiments of the present disclosure, the first-stage reaction is conducted at a temperature of −10° C. to 10° C., and preferably 0° C. In some embodiments of the present disclosure, the first-stage reaction is conducted for less than or equal to 2 h, and preferably 1 h. In some embodiments of the present disclosure, the second-stage reaction is conducted at a temperature of 0° C. to 50° C., and preferably room temperature. In some embodiments of the present disclosure, the second-stage reaction is conducted for 1 h to 24 h, and preferably 12 h to 24 h. In some embodiments of the present disclosure, the carbon-boron bond oxidation is conducted under stirring.

In the present disclosure, the method further includes the following steps after the carbon-boron bond oxidation is completed: subjecting a resulting product system to extraction, removing the organic solvent from a resulting organic phase, and subjecting a resulting crude product to separation by column chromatography to obtain the intermediate C of the L-6-HTP derivative. In some embodiments of the present disclosure, water and ethyl acetate are added to the product system in sequence, and a resulting system is subjected to extraction. In some embodiments of the present disclosure, after the extraction, drying is conducted, and a desiccant for the drying is anhydrous sodium sulfate. In some embodiments of the present disclosure, after the drying, filtration is conducted to remove the organic solvent in a filtrate to obtain the crude product. In some embodiments of the present disclosure, a process for removing the organic solvent is vacuum distillation, and the organic solvent can be recycled. In some embodiments of the present disclosure, a silica gel for the separation is 200-300 mesh silica gel. In some embodiments of the present disclosure, the separation includes a first-stage separation and a second-stage separation in sequence. In some embodiments of the present disclosure, a first eluent used in the first-stage separation is a mixture of petroleum ether and ethyl acetate. In some embodiments of the present disclosure, a volume ratio of the petroleum ether to the ethyl acetate in the first eluent is 95:5. In some embodiments of the present disclosure, a second eluent used in the second-stage separation is a mixture of petroleum ether and ethyl acetate. In some embodiments of the present disclosure, a volume ratio of the petroleum ether to the ethyl acetate in the second eluent is 92:8. In some embodiments of the present disclosure, the 200-300 mesh silica gel is added to a glass column, then the crude product is added thereto, eluted with the first eluent, an eluate of a first band is collected, the organic solvent is recycled by vacuum distillation to obtain impurities, then the second eluent is used for elution, an eluate of a second band is collected, and the organic solvent is recycled by vacuum distillation to obtain a light yellow oily liquid, which is the intermediate C of the L-6-HTP derivative.

The present disclosure further provides a method for preparing an intermediate D of an L-6-HTP derivative, including the following steps:

preparing the intermediate C of the L-6-HTP derivative by the method described in the above technical solution; and subjecting the intermediate C of the L-6-HTP derivative to hydroxyl-targeted benzyl protection to obtain the intermediate D of the L-6-HTP derivative;

where the intermediate D of the L-6-HTP derivative has a structure shown in Formula 5:

Formula 5

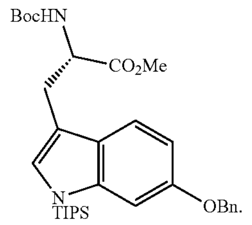

In some embodiments of the present disclosure, the method for preparing the intermediate C of the L-6-HTP derivative is consistent with that in the above technical solution, and will not be repeated here.

In the present disclosure, after the intermediate C of the L-6-HTP derivative is obtained, the intermediate C of the L-6-HTP derivative is subjected to hydroxyl-targeted benzyl protection to obtain an intermediate D of the L-6-HTP derivative. In some embodiments of the present disclosure, a benzyl reagent for the hydroxyl-targeted benzyl protection includes benzyl bromide. In some embodiments of the present disclosure, the hydroxyl-targeted benzyl protection is conducted in the presence of potassium iodide and potassium carbonate. In some embodiments of the present disclosure, a molar ratio of the intermediate C of the L-6-HTP derivative, the benzyl bromide, the potassium iodide, and the potassium carbonate is in a range of 1:1-5:0-1:1-5, and preferably 1:1.2:0.05:2. In some embodiments of the present disclosure, the hydroxyl-targeted benzyl protection is conducted in the presence of an organic solvent. In some embodiments of the present disclosure, the organic solvent is one or more selected from the group consisting of acetonitrile, dioxane, and methanol, and preferably the acetonitrile. In some embodiments of the present disclosure, a dosage ratio of the organic solvent to the intermediate C of the L-6-HTP derivative is in a range of 0.5-2 L:0.1 mol, and preferably 1-2 L:0.1 mol.

In some embodiments of the present disclosure, the intermediate C of the L-6-HTP derivative is dissolved in the organic solvent, then the potassium carbonate, the potassium iodide and the benzyl bromide are added in sequence, and a resulting system is subjected to the hydroxyl-targeted benzyl protection. In some embodiments of the present disclosure, the hydroxyl-targeted benzyl protection is conducted at a temperature of 30° C. to 100° C. In some embodiments of the present disclosure, the hydroxyl-targeted benzyl protection is conducted under reflux conditions. In some embodiments of the present disclosure, the hydroxyl-targeted benzyl protection is conducted at 70° C. In some embodiments of the present disclosure, the hydroxyl-targeted benzyl protection is conducted for 2 h to 24 h, and preferably 12 h. In some embodiments of the present disclosure, the hydroxyl-targeted benzyl protection is conducted under stirring.

In the present disclosure, the method further includes the following steps after the hydroxy-targeted benzyl protection is completed: subjecting a resulting product system to extraction, removing the organic solvent from a resulting organic phase, and subjecting a resulting crude product to separation by column chromatography to obtain the intermediate D of the L-6-HTP derivative. In some embodiments of the present disclosure, water and ethyl acetate are added to the product system in sequence, and a resulting system is subjected to extraction. In some embodiments of the present disclosure, after the extraction, drying is conducted, and a desiccant for the drying is anhydrous sodium sulfate. In some embodiments of the present disclosure, after the drying, filtration is conducted to remove the organic solvent in a filtrate to obtain the crude product. In some embodiments of the present disclosure, a process for removing the organic solvent is vacuum distillation, and the organic solvent can be recycled. In some embodiments of the present disclosure, a silica gel for the separation is preferably 200-300 mesh silica gel. In some embodiments of the present disclosure, an eluent for the separation is a mixture of petroleum ether and ethyl acetate. In some embodiments of the present disclosure, a volume ratio of the petroleum ether to the ethyl acetate in the eluent is in a range of 90:10. In some embodiments of the present disclosure, the 200-300 mesh silica gel is added to a glass column then the crude product is added thereto, eluted with the eluent, an eluate of a first band is collected, and the organic solvent is recycled by vacuum distillation to obtain a light yellow oily liquid, which is the intermediate D of the L-6-HTP derivative.

The present disclosure further provides a method for preparing an intermediate E of an L-6-HTP derivative, including the following steps:

- preparing the intermediate D of the L-6-HTP derivative by the method described in the above technical solution; and
- subjecting the intermediate D of the L-6-HTP derivative to TIPS protective group removal to obtain the intermediate E of the L-6-HTP derivative;
- where the intermediate E of the L-6-HTP derivative has a structure shown in Formula 6:

Formula 6

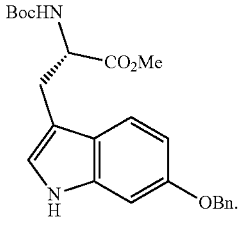

In some embodiments of the present disclosure, the method for preparing the intermediate D of the L-6-HTP derivative is consistent with that in the above technical solution, and will not be repeated here.

In the present disclosure, after the intermediate D of the L-6-HTP derivative is obtained, the intermediate D of the L-6-HTP derivative is subjected to TIPS protective group removal to obtain an intermediate E of the L-6-HTP derivative. In some embodiments of the present disclosure, the TIPS protective group removal is conducted in the presence of TBAF. In some embodiments of the present disclosure, a molar ratio of the intermediate D of the L-6-HTP derivative to the TBAF is in a range of 1:1-5, and preferably 1:1.5. In some embodiments of the present disclosure, the TIPS protective group removal is conducted in the presence of an organic solvent. In some embodiments of the present disclosure, the organic solvent is one or more selected from the group consisting of THF, methanol, and dioxane, and preferably the THF. In some embodiments of the present disclosure, a dosage ratio of the organic solvent to the intermediate D of the L-6-HTP derivative is in a range of 0.5-2 L:1 mol, and preferably 1 L:1 mol.

In some embodiments of the present disclosure, the intermediate D of the L-6-HTP derivative is dissolved in the organic solvent, then the TBAF is added, and a resulting system is subjected to the TIPS protective group removal. In some embodiments of the present disclosure, the TIPS protective group removal is conducted at a temperature of 0° C. to 50° C., and preferably room temperature. In some embodiments of the present disclosure, the TIPS protective group removal is conducted for 0.2 h to 6 h, and preferably 0.5 h. In some embodiments of the present disclosure, the TIPS protective group removal is conducted under stirring.

In the present disclosure, the method further includes the following steps after the TIPS protective group removal is completed: subjecting a resulting product system to extraction, removing the organic solvent from a resulting organic phase, and subjecting a resulting crude product to separation by column chromatography to obtain the intermediate E of the L-6-HTP derivative. In some embodiments of the present disclosure, a saturated ammonium chloride solution and ethyl acetate are added to the product system in sequence, and a resulting system is subjected to extraction. In some embodiments of the present disclosure, after the extraction, drying is conducted, and a desiccant for the drying is anhydrous sodium sulfate. In some embodiments of the present disclosure, after the drying, filtration is conducted to remove the organic solvent in a filtrate to obtain the crude product. In some embodiments of the present disclosure, a process for removing the organic solvent is vacuum distillation, and the organic solvent can be recycled. In some embodiments of the present disclosure, a silica gel for the separation is 200-300 mesh silica gel. In some embodiments of the present disclosure, an eluent for the separation is a mixture of petroleum ether and ethyl acetate. In some embodiments of the present disclosure, a volume ratio of the petroleum ether to the ethyl acetate in the eluent is in a range of 95:5. In some embodiments of the present disclosure, the 200-300 mesh silica gel is added to a glass column then the crude product is added thereto, eluted with the eluent, an eluate of a first band is collected, and the organic solvent is recycled by vacuum distillation to obtain a light yellow oily liquid, which is the intermediate E of the L-6-HTP derivative.

The present disclosure further provides a method for preparing an intermediate F of an L-6-HTP derivative, including the following steps:

- preparing the intermediate E of the L-6-HTP derivative by the method described in the above technical solution; and
- subjecting the intermediate E of the L-6-HTP derivative to tert-butoxycarbonyl (Boc) protective group removal to obtain the intermediate F of the L-6-HTP derivative;
- where the intermediate F of the L-6-HTP derivative has a structure shown in Formula 7:

Formula 7

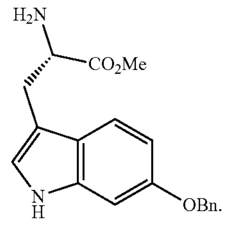

In some embodiments of the present disclosure, the method for preparing the intermediate E of the L-6-HTP derivative is consistent with that in the above technical solution, and will not be repeated here.

In the present disclosure, after the intermediate E of the L-6-HTP derivative is obtained, the intermediate E of the L-6-HTP derivative is subjected to Boc protective group removal to obtain an intermediate F of the L-6-HTP derivative. In some embodiments of the present disclosure, the Boc protective group removal is conducted in the presence of TFA. In some embodiments of the present disclosure, a molar ratio of the TFA to the intermediate E of the L-6-HTP derivative is in a range of 0.5-3 L:0.1 mol, and preferably 1-3 L:0.1 mol. In some embodiments of the present disclosure, the Boc protective group removal is conducted in the presence of an organic solvent. In some embodiments of the present disclosure, the organic solvent is one or more selected from the group consisting of dichloromethane (DCM), ethyl acetate, and methanol, and preferably the DCM. In some embodiments of the present disclosure, a volume ratio of the organic solvent to the TFA is in a range of 0-6:3, and preferably 1:3.

In some embodiments of the present disclosure, the intermediate E of the L-6-HTP derivative is dissolved in the organic solvent, then the TFA is added, and a resulting system is subjected to the Boc protective group removal. In some embodiments of the present disclosure, the Boc protective group removal is conducted at a temperature of 0° C. to 50° C., and preferably room temperature. In some embodiments of the present disclosure, the Boc protective group removal is conducted for 0.2 h to 6 h, and preferably 0.5 h. In some embodiments of the present disclosure, the Boc protective group removal is conducted under stirring.

In the present disclosure, the method further includes the following steps after the Boc protective group removal is completed: removing the organic solvent from a resulting product, and subjecting a resulting crude product to separation by column chromatography to obtain the intermediate F of the L-6-HTP derivative. In some embodiments of the present disclosure, a process for removing the organic solvent is vacuum distillation, and the organic solvent can be recycled. In some embodiments of the present disclosure, a silica gel for the separation is 200-300 mesh silica gel. In some embodiments of the present disclosure, an eluent for the separation is a mixture of DCM and methanol. In some embodiments of the present disclosure, a volume ratio of the DCM to the methanol in the eluent is in a range of 98:2. In some embodiments of the present disclosure, the 200-300 mesh silica gel is added to a glass column and then the crude product is added thereto, eluted with the eluent, an eluate of a first band is collected, and the organic solvent is recycled by vacuum distillation to obtain a light yellow oily liquid, which is the intermediate F of the L-6-HTP derivative.

The present disclosure further provides a method for preparing an L-6-HTP derivative, including the following steps:

preparing the intermediate F of the L-6-HTP derivative by the method described in the above technical solution; and subjecting the intermediate F of the L-6-HTP derivative to methyl ester hydrolysis and amino-targeted 9-fluorenylmethoxycarbonyl (Fmoc) protection to obtain the L-6-HTP derivative;

where the L-6-HTP derivative has a structure shown in Formula 8:

Formula 8

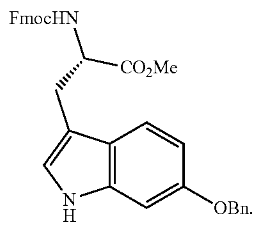

In some embodiments of the present disclosure, the method for preparing the intermediate F of the L-6-HTP derivative is consistent with that in the above technical solution, and will not be repeated here.

In the present disclosure, after the intermediate F of the L-6-HTP derivative is obtained, the intermediate F of the L-6-HTP derivative is subjected to methyl ester hydrolysis and amino-targeted Fmoc protection to obtain the L-6-HTP derivative. In some embodiments of the present disclosure, the intermediate F of the L-6-HTP derivative is subjected to the methyl ester hydrolysis and the amino-targeted Fmoc protection in sequence, which are described in detail, respectively.

In some embodiments of the present disclosure, the methyl ester hydrolysis is conducted in the presence of sodium hydroxide. In some embodiments of the present disclosure, a molar ratio of the intermediate F of the L-6-HTP derivative to the sodium hydroxide is in a range of 1:1-10, and preferably 1:5. In some embodiments of the present disclosure, the methyl ester hydrolysis is conducted in the presence of an organic solvent and water. In some embodiments of the present disclosure, the organic solvent is one or more selected from the group consisting of THF, methanol, and dioxane. In some embodiments of the present disclosure, a dosage ratio of the organic solvent, the water, and the intermediate F of the L-6-HTP derivative is in a range of 0.5-3 L:0.5-2 L:1 mol, and preferably 1 L:1 L:1 mol.

In some embodiments of the present disclosure, the intermediate F of the L-6-HTP derivative is dissolved in the organic solvent, then the sodium hydroxide and the water are added in sequence, and a resulting system is subjected to the methyl ester hydrolysis. In some embodiments of the present disclosure, the methyl ester hydrolysis is conducted at a temperature of 0° C. to 50° C., and preferably room temperature. In some embodiments of the present disclosure, the methyl ester hydrolysis is conducted for 0.5 h to 6 h, and preferably 1 h. In some embodiments of the present disclosure, the methyl ester hydrolysis is conducted under stirring.

In the present disclosure, the method further includes the following steps after the methyl ester hydrolysis is completed: subjecting a resulting product system to extraction, removing the organic solvent from a resulting organic phase, and subjecting a resulting crude product to the amino-targeted Fmoc protection. In some embodiments of the present disclosure, water and ethyl acetate are added to the product system in sequence, and a resulting system is subjected to extraction. In some embodiments of the present disclosure, after the extraction, drying is conducted, and a desiccant for the drying is anhydrous sodium sulfate. In some embodiments of the present disclosure, after the drying, filtration is conducted to remove the organic solvent in a filtrate to obtain the crude product. In some embodiments of the present disclosure, a process for removing the organic solvent is vacuum distillation, and the organic solvent can be recycled.

In some embodiments of the present disclosure, a raw material for the amino-targeted Fmoc protection includes Fmoc-Cl, and the amino-targeted Fmoc protection is conducted in the presence of sodium carbonate. In some embodiments of the present disclosure, based on a dosage of the intermediate F of the L-6-HTP derivative, a molar ratio of the intermediate F of the L-6-HTP derivative, the Fmoc-Cl, and the sodium carbonate is in a range of 1:1-3:1-3, and preferably 1:1.3:1.5. In some embodiments of the present disclosure, the amino-targeted Fmoc protection is conducted in the presence of an organic solvent and water. In some embodiments of the present disclosure, the organic solvent is one or more selected from the group consisting of 1,4-dioxane, THF, and methanol, and preferably the 1,4-dioxane. In some embodiments of the present disclosure, based on a dosage of the intermediate F of the L-6-HTP derivative, a dosage ratio of the organic solvent, the water, and the intermediate F of the L-6-HTP derivative is in a range of 0.5-3 L:0.5-2 L:1 mol, and preferably 1 L:1 L:1 mol.

In some embodiments of the present disclosure, the Fmoc-Cl is dissolved in a part of the organic solvent for the amino-targeted Fmoc protection to obtain an Fmoc-Cl solution; the crude product obtained after the methyl ester hydrolysis is dissolved in the remaining organic solvent for the amino-targeted Fmoc protection, the sodium carbonate is added thereto, the Fmoc-Cl solution is added dropwise, then the water is added, and a resulting system is subjected to the amino-targeted Fmoc protection. In some embodiments of the present disclosure, the amino-targeted Fmoc protection is conducted at a temperature of 0° C. to 50° C., and preferably a room temperature. In some embodiments of the present disclosure, the amino-targeted Fmoc protection is conducted for 1 h to 24 h, and preferably 4 h. In some embodiments of the present disclosure, the amino-targeted Fmoc protection is conducted under stirring.

In some embodiments of the present disclosure, the method further includes the following steps after the amino-targeted Fmoc protection is completed: subjecting a resulting product system to extraction, removing the organic solvent from a resulting organic phase, and subjecting a resulting crude product to separation by column chromatography to obtain the L-6-HTP derivative. In some embodiments of the present disclosure, water and ethyl acetate are added to the product system in sequence, and a resulting system is subjected to extraction. In some embodiments of the present disclosure, after the extraction, drying is conducted, and a desiccant for the drying is anhydrous sodium sulfate. In some embodiments of the present disclosure, after the drying, filtration is conducted to remove the organic solvent in a filtrate to obtain the crude product. In some embodiments of the present disclosure, a process for removing the organic solvent is vacuum distillation, and the organic solvent can be recycled. In some embodiments of the present disclosure, a silica gel for the separating is 200-300 mesh silica gel. In some embodiments of the present disclosure, the separating includes I-stage separation and II-stage separation in sequence. In some embodiments of the present disclosure, a I eluent used in the I-stage separation is a mixture of DCM and methanol. In some embodiments of the present disclosure, a volume ratio of the DCM to the methanol in the I eluent is 99:1. In some embodiments of the present disclosure, a II eluent used in the II-stage separation is a mixture of DCM and methanol. In some embodiments of the present disclosure, a volume ratio of the DCM to the methanol in the II eluent is 98:2. In some embodiments of the present disclosure, the 200-300 mesh silica gel is added to a glass column, then the crude product is added thereto, eluted with the I eluent, an eluate of a first band is collected, the organic solvent is recycled by vacuum distillation to obtain impurities, then the II eluent is used for elution, an eluate of a first band is collected, and the organic solvent is recycled by vacuum distillation to obtain a colorless solid, which is the L-6-HTP derivative.

The present disclosure further provides an intermediate for synthesizing an L-6-HTP derivative, including a compound having structures shown in Formula 4, Formula 5, or Formula 6:

Formula 4

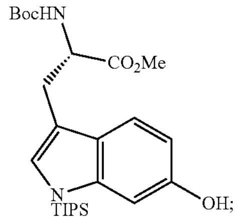

Formula 5

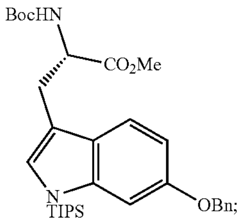

Formula 6

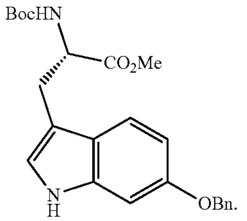

The technical solutions of the present disclosure will be clearly and completely described below with reference to the examples of the present disclosure. Apparently, the described examples are merely a part rather than all of the examples of the present disclosure. All other examples obtained by a person of ordinary skill in the art based on the examples of the present disclosure without creative efforts shall fall within the scope of the present disclosure.

Example 1 Synthesis of Compound A6-2

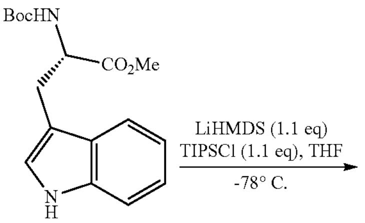

A6-0

-continued

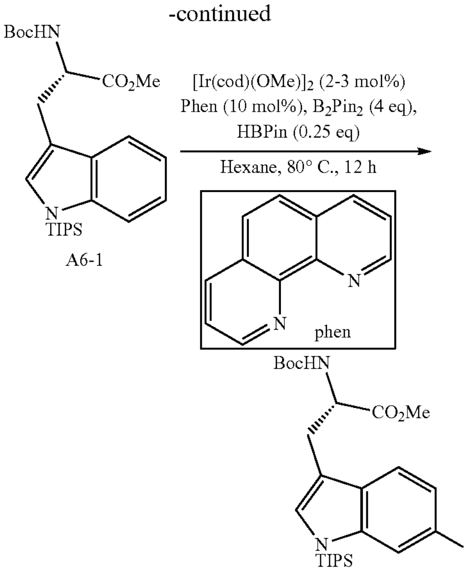

A6-1

A6-2

Under nitrogen protection, 47.7 g (0.15 mol) of a compound A6-0 was added into a reaction flask, 300 mL of dry THF was added thereto. A resulting mixture was stirred at −78° C. for 15 min to obtain a solution of the compound A6-0. 139 mL of a solution of LiHMDS (0.18 mol) with a concentration of 1.3 mol/L in THF was added dropwise into the solution of the compound A6-0. A resulting mixture was subjected to reaction at −78° C. for 1 h. 41 mL of a solution of TIPSCl (34.7 g, 0.18 mol) in THF was added dropwise to a resulting reaction solution with a syringe. A resulting mixture was heated to room temperature and subjected to reaction for 1 h. After the reaction was completed, 100 mL of a saturated $NH_4Cl$ solution was added to a resulting system to quench the reaction. A resulting product was subjected to extraction 3 times with 300 mL of ethyl acetate. Resulting organic phases were combined, dried over anhydrous sodium sulfate, and filtered, and the solvent was removed by vacuum distillation to obtain a crude product. The crude product was subjected to separation by column chromatography. Specifically, 200-300 mesh silica gel was added to a glass column and then the crude product was added thereto. Elution was conducted using a mixed solvent of petroleum ether and ethyl acetate in a volume ratio of 95:5 as an eluent. A resulting eluate was collected, and subjected to vacuum distillation to remove the solvent to obtain 63.55 g of a white solid powder, which was a compound A6-1, with a yield of 89%.

NMR data of the compound A6-1 are as follows:

$^1$H NMR (600 MHz, $CDCl_3$) δ 7.53 (d, J=7.5 Hz, 1H), 7.47 (d, J=8.0 Hz, 1H), 7.13 (dt, J=14.7, 7.0 Hz, 2H), 7.03 (s, 1H), 5.06 (d, J=7.5 Hz, 1H), 4.65 (d, J=6.9 Hz, 1H), 3.63 (s, 3H), 3.28 (s, 2H), 1.68 (dq, J=15.0, 7.5 Hz, 3H), 1.43 (s, 9H), 1.14 (dd, J=7.6, 2.0 Hz, 18H). $^{13}$C NMR (151 MHz, $CDCl_3$) δ 172.8, 155.3, 141.4, 131.2, 129.9, 121.7, 119.8, 118.8, 114.1, 112.2, 79.8, 54.2, 52.2, 28.5, 28.2, 18.3, 12.9.

In a glove box, (1,5-cyclooctadiene)(methoxy)iridium(I) dimer ($[Ir(cod)(OMe)]_2$, 3.3 g, 5 mmol) and 1,10-phenanthroline (phen, 1.8 g, 10 mmol) were added to a round-bottom flask, and then 300 mL of n-hexane was added to the round-bottom flask. A resulting system was subjected to complexation at room temperature for 10 min. Pinacolborane (HBPin, 3.2 g, 25 mmol), the compound A6-1 (47.6 g, 0.1 mol), and 300 mL of n-hexane were added to the round-bottom flask and stirred for 5 min, followed by adding bis(pinacolato)diboron ($B_2Pin_2$, 104.0 g, 0.4 mol) and 200 mL of n-hexane. The round-bottom flask was sealed with a bottle cap, and removed from the glove box. A resulting system in sealed round-bottom flask was subjected to reaction at 80° C. for 24 h. After the reaction was completed, 200 mL of a saturated $NaHCO_3$ solution was added to quench the reaction. A resulting product was subjected to extraction 3 times with 500 mL of ethyl acetate. Resulting organic phases were combined, washed 3 times with saturated ammonium chloride solution, dried over anhydrous sodium sulfate, filtered, and the solvent was removed under reduced pressure to obtain a crude product. The crude product was subjected to separation by column chromatography. Specifically, 200-300 mesh silica gel was added to a glass column and then the crude product was added thereto. Elution was conducted using a mixed solvent of petroleum ether and ethyl acetate in a volume ratio of 95:5 as an eluent. A resulting eluate was collected, and subjected to vacuum distillation to remove the solvent to obtain 47.4 g of a light yellow oily liquid, which was the compound A6-2, with a yield of 79%.

NMR data of the compound A6-2 are as follows:

$^1$H NMR (500 MHz, $CDCl_3$) δ 7.92 (s, 1H), 7.55 (d, J=8.8 Hz, 1H), 7.51 (d, J=8.8 Hz, 1H), 7.08 (s, 1H), 5.04 (d, J=8.1 Hz, 1H), 4.65-4.63 (m, 1H), 3.62 (s, 3H); 3.27 (d, J=5.5 Hz, 2H), 1.71-1.68 (m, 3H), 1.43 (s, J=6.3 Hz, 9H), 1.35 (s, 12H), 1.13 (d, J=7.2 Hz, 18H); $^{13}$C NMR (151 MHz, $CDCl_3$) δ 172.7, 155.2, 141.0, 133.6, 131.4, 125.7, 121.0, 118.0, 113.5, 112.2, 83.5, 79.8, 54.3, 52.3, 28.5, 28.1, 25.0, 18.3, 13.0.

Example 2 Synthesis of Compound A6-3

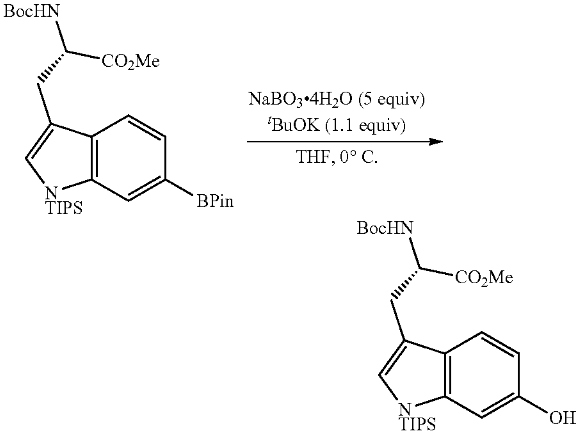

66 g (0.1 mol) of the compound A6-2 was added to a reaction flask, and then 1 L of THF was added to fully dissolve the compound A6-2. The reaction flask was transferred to a 0° C. ice bath for 3 min, 12.3 g (0.11 mol) of KTB (tBuOK), 76.9 g (0.5 mol) of sodium perborate tetrahydrate ($NaBO_3 \cdot 4H_2O$), and 3 L of water were added to the reaction flask in sequence. A resulting system was subjected to reaction under stirring at 0° C. for 1 h. A resulting product was transferred to room temperature (25° C.), and subjected to reaction for 24 h. After the reaction was completed, 1 L of water and 1 L of ethyl acetate were added to a resulting product system in sequence. A resulting system was subjected to extraction 3 times with ethyl acetate to obtain organic phases, the organic phases were combined, dried over anhydrous sodium sulfate for 2 min, and filtered, and a resulting filtrate was subjected to vacuum distillation and the solvent was recovered to obtain a crude product. The crude product was subjected to separation by column chromatography. Specifically, 200-300 mesh silica gel was added to a glass column and then the crude product was added thereto. Elution was conducted using a mixed solvent of petroleum ether and ethyl acetate in a volume ratio of 95:5 as an eluent. A resulting eluate of the first band was collected, and the solvent was recovered by vacuum distillation to obtain impurities. A mixed solvent of petroleum ether and ethyl acetate in a volume ratio of 92:8 was used as an eluent. The impurities were subjected to elution with the mixed solvent of petroleum ether and ethyl, a resulting eluate of the second band was collected, and the solvent was recovered by vacuum distillation to obtain 57.0 g of a light yellow oily liquid, which was the compound A6-3, with a yield of 85%.

A chemical name of the compound A6-3 is (S)-3-(6-(hydroxy)-1-(triisopropylsilyl)-1H-indol-3-yl)-2-((tert-butyloxycarbonyl)amino)methyl propionate, and NMR data thereof are as follows:

$^{1}$H NMR (600 MHz, DMSO) δ 8.92 (s, 1H), 7.26 (d, J=8.4 Hz, 1H), 7.15 (d, J=7.7 Hz, 1H), 7.00 (s, 1H), 6.89 (s, 1H), 6.60 (d, J=8.4 Hz, 1H), 4.26-4.18 (m, 1H), 3.58 (s, 3H), 3.05 (dd, J=14.5, 4.9 Hz, 1H), 2.93 (dd, J=14.3, 9.5 Hz, 1H), 1.64 (dt, J=14.9, 7.4 Hz, 3H), 1.33 (s, 9H), 1.11-1.07 (m, 18H). $^{13}$C NMR (151 MHz, DMSO) δ 172.9, 155.20, 153.2, 141.8, 127.6, 123.7, 118.2, 112.8, 109.5, 99.4, 78.0, 53.9, 51.7, 28.1, 26.7, 17.9, 12.1.

Example 3 Synthesis of a Compound A6-4

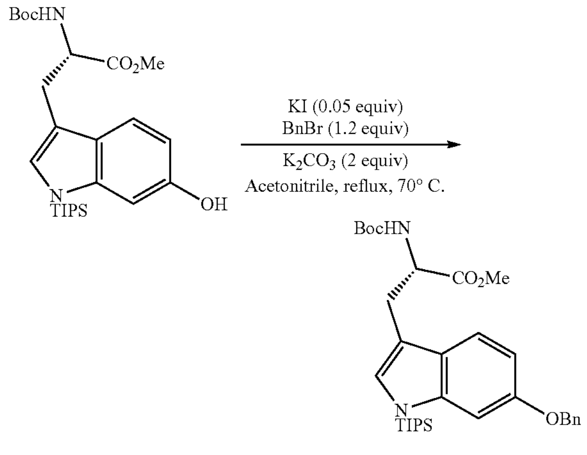

49 g (0.1 mol) of the compound A6-3 was added to a reaction flask, 2 L of acetonitrile was added to fully dissolve the compound A6-3, and then 27.7 g (0.2 mol) of potassium carbonate ($K_2CO_3$), 0.9 g (0.005 mol) of potassium iodide (KI), and 20.5 g (0.12 mol) of benzyl bromide (BnBr) were added in sequence. A resulting mixture was subjected to reaction under stirring and reflux at 70° C. for 12 h. After the reaction was completed, 1 L of water and 1 L of ethyl acetate were added to a resulting product system in sequence. A resulting system was subjected to extraction 3 times with ethyl acetate to obtain organic phases. The organic phases were combined, dried over anhydrous sodium sulfate for 2 min, and filtered, and a resulting filtrate was subjected to vacuum distillation and the solvent was recovered to obtain a crude product. The crude product was subjected to separation by column chromatography. Specifically, 200-300 mesh silica gel was added to a glass column and then the crude product was added thereto. Elution was conducted using a mixed solvent of petroleum ether and ethyl acetate in a volume ratio of 90:10 as an eluent. A resulting eluate of the first band was collected, and the solvent was recovered by vacuum distillation to obtain 52.5 g of a light yellow oily liquid, which was the compound A6-4, with a yield of 90%.

A chemical name of the compound A6-4 is (S)-3-(6-(benzyloxy)-1-(triisopropylsilyl)-1H-indol-3-yl)-2-((tert-butyloxycarbonyl)amino)methyl propionate, and NMR data thereof are as follows:

$^{1}$H NMR (600 MHz, $CDCl_3$) δ 7.45 (d, J=7.5 Hz, 2H), 7.41-7.37 (m, 3H), 7.31 (t, J=7.3 Hz, 1H), 6.96 (s, 1H), 6.91-6.89 (m, 2H), 5.13 (s, 1H), 5.07 (s, 1H), 4.63 (d, J=4.9 Hz, 1H), 3.64 (s, 3H), 3.23 (s, 2H), 1.55 (dt, J=14.8, 7.4 Hz, 3H), 1.44 (s, 9H), 1.09 (d, J=7.6 Hz, 18H). $^{13}$C NMR (151 MHz, $CDCl_3$) δ 173.0, 155.4, 152.1, 142.3, 128.5, 125.5, 119.0, 111.9, 109.7, 100.2, 80.0, 54.1, 52.3, 28.5, 27.0, 18.3, 12.9.

Example 4 Synthesis of a Compound A6-5

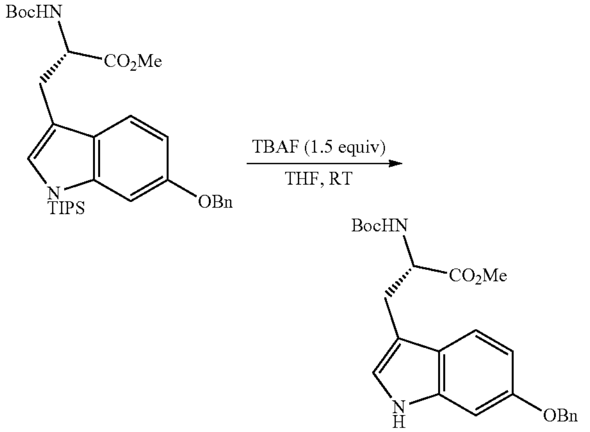

58 g (0.1 mol) of the compound A6-4 was added to a reaction flask, and then 0.1 L of THF was added to fully dissolve the compound A6-4. After 3 min, 39 g (0.15 mol) of TBAF was added thereto. A resulting mixture was subjected to reaction under stirring at room temperature for 30 min. After the reaction was completed, 0.1 L of a saturated ammonium chloride ($NH_4Cl$) solution and 0.1 L of ethyl acetate were added to a resulting product system in sequence. A resulting system was subjected to extraction 3 times with saturated ammonium chloride solution to obtain organic phases, and 0.1 L of the saturated ammonium chloride solution was used each time. The organic phases were combined, dried over anhydrous sodium sulfate for 2 min, and filtered, and a resulting filtrate was subjected to vacuum distillation and the solvent was recovered to obtain a crude product. The crude product was subjected to separation by column chromatography. Specifically, 200-300 mesh silica gel was added to a glass column and then the crude product was added thereto. Elution was conducted using a mixed solvent of petroleum ether and ethyl acetate in a volume ratio of 95:5 as an eluent. A resulting eluate of the first band was collected, and the solvent was recovered by vacuum distillation to obtain 39.0 g of a light yellow oily liquid, which was the compound A6-5, with a yield of 92%.

A chemical name of the compound A6-5 is (S)-3-(6-(benzyloxy)-1H-indol-3-yl)-2-((tert-butyloxycarbonyl) amino)methyl propionate, and NMR data thereof are as follows:

$^1$H NMR (600 MHz, $CDCl_3$) δ 8.27 (s, 1H), 7.46 (d, J=7.4 Hz, 2H), 7.43 (d, J=8.7 Hz, 1H), 7.39 (t, J=7.6 Hz, 2H), 7.33 (t, J=7.3 Hz, 1H), 6.88 (dt, J=6.0, 3.0 Hz, 1H), 6.86 (d, J=1.8 Hz, 1H), 6.84 (s, 1H), 5.07 (s, 2H), 4.65 (dd, J=12.8, 5.4 Hz, 1H), 3.67 (d, J=6.3 Hz, 3H), 3.25 (d, J=4.6 Hz, 2H), 1.45 (s, 9H). $^{13}$C NMR (151 MHz, $CDCl_3$) δ 172.9, 155.7, 155.4, 137.5, 136.9, 128.6, 127.9, 127.6, 122.4, 121.8, 119.4, 110.4, 109.9, 96.1, 79.9, 77.1, 70.6, 54.3, 52.3, 28.4, 28.09.

Example 5 Synthesis of a Compound A6-6

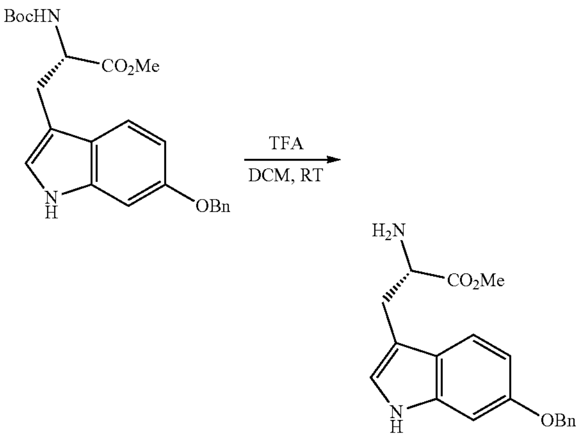

42.4 g (0.1 mol) of the compound A6-5 was added to a reaction flask, 1 L of DCM was added to fully dissolve the compound A6-5, and then 3 L of TFA was added thereto. A resulting mixture was subjected to reaction under stirring at room temperature for 30 min. After the reaction was completed, a resulting product was subjected to vacuum distillation and the solvent was recovered to obtain a crude product. The crude product was subjected to separation by column chromatography. Specifically, 200-300 mesh silica gel was added to a glass column and then the crude product was added thereto. Elution was conducted using a mixed solvent of DCM and methanol in a volume ratio of 98:2 as an eluent. A resulting eluate of the first band was collected, and the solvent was recovered by vacuum distillation to obtain 27.4 g of a light yellow oily liquid, which was the compound A6-6, with a yield of 85%.

A chemical name of the compound A6-6 Is (S)-2-amino-3-(6-(benzyloxy)-1H-indol-3-yl)methyl propionate, and NMR data thereof are as follows:

$^1$H NMR (600 MHz, DMSO) δ 10.68 (s, 1H), 7.47 (d, J=7.5 Hz, 2H), 7.41-7.36 (m, 3H), 7.32 (t, J=7.2 Hz, 1H), 6.99 (s, 1H), 6.94 (s, 1H), 6.74 (dd, J=8.6, 1.9 Hz, 1H), 5.10 (s, 2H), 3.62 (dd, J=8.7, 3.5 Hz, 1H), 3.56 (s, 3H), 3.36 (s, 2H), 2.99 (dd, J=14.0, 6.0 Hz, 1H), 2.92 (dd, J=14.1, 6.3 Hz, 1H). $^{13}$C NMR (151 MHz, DMSO) δ 175.7, 154.5, 137.7, 136.7, 128.4, 127.6, 127.5, 122.4, 122.1, 118.9, 109.9, 109.2, 96.0, 69.6, 55.2, 51.4, 30.8.

Example 6 Synthesis of a Compound A6-7

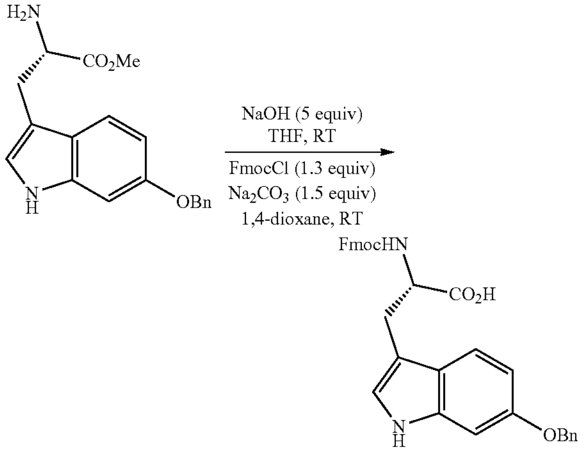

32.4 g (0.1 mol) of the compound A6-6 was added to a reaction flask, 0.1 L of THF was added to fully dissolve the compound A6-6, and then 20 g (0.5 mol) of sodium hydroxide (NaOH) and 0.1 L of water were added in sequence. A resulting mixture was subjected to reaction under stirring at room temperature for 1 h. After the reaction was completed, 0.1 L of water and 0.1 L of ethyl acetate were added to a resulting product system in sequence. A resulting system was subjected to extraction 3 times with ethyl acetate to obtain organic phases. The organic phases were combined, dried over anhydrous sodium sulfate for 2 min, and filtered, and a resulting filtrate was subjected to vacuum distillation and the solvent was recovered to obtain a crude product.

The crude product was transferred to a reaction flask, 75 mL of 1,4-dioxane was added to fully dissolve the crude product, after which 15.9 g (0.15 mol) of sodium carbonate ($Na_2CO_3$), then a solution of Fmoc-Cl (33.7 g, 0.13 mol) in 1,4-dioxane (25 mL) was added dropwise, and finally 0.1 L of water was added. A resulting mixture was subjected to reaction under stirring at room temperature for 4 h. After the reaction was completed, 1 L of water and 2 L of ethyl acetate were added to a resulting product system in sequence. A resulting system was subjected to extraction 3 times with ethyl acetate to obtain organic phases. The organic phases were combined, dried over anhydrous sodium sulfate for 2 min, and filtered, and a resulting filtrate was subjected to vacuum distillation and the solvent was recovered to obtain a crude product. The crude product was subjected to separation by column chromatography. Specifically, 200-300 mesh silica gel was added to a glass column and then the crude product was added thereto. Elution was conducted using a mixed solvent of DCM and methanol in a volume ratio of 99:1 as an eluent. A resulting eluate of the first band was collected, and the solvent was recovered by vacuum distillation to obtain impurities. A mixed solvent of DCM and methanol in a volume ratio of 98:2 was used as an eluent. The impurities were subjected to elution with the mixed solvent of DCM and methanol, a resulting eluate of the first band was collected, and the solvent was recovered by vacuum distillation to obtain 44.0 g of a colorless solid, which was the compound A6-7, with a yield of 80%.

A chemical name of the compound A6-7 is (S)-2-((((9H-fluoren-9-yl)methoxy)carbonyl)amino)-3-(6-(benzyloxy)-1H-indol-3-yl)propanoic acid, and NMR data thereof are as follows:

$^1H$ NMR (600 MHz, DMSO) δ 12.70 (s, 1H), 10.68 (s, 1H), 7.88 (d, J=6.9 Hz, 2H), 7.68 (dd, J=12.8, 7.2 Hz, 2H), 7.51-7.43 (m, 3H), 7.44-7.35 (m, 4H), 7.35-7.24 (m, 3H), 7.06 (s, 1H), 6.94 (s, 1H), 6.75 (d, J=7.8 Hz, 1H), 5.11 (s, 2H), 4.36-4.04 (m, 4H), 3.19 (d, J=10.7 Hz, 1H), 3.07-2.96 (m, 1H). $^{13}C$ NMR (151 MHz, DMSO) δ 173.7, 155.9, 154.5, 143.8, 140.7, 137.7, 136.7, 128.4, 127.6, 127.4, 127.1, 125.3, 125.3, 122.4, 121.9, 120.1, 118.8, 110.3, 109.2, 96.1, 69.6, 65.6, 54.9, 46.6, 27.0.

As shown in the above examples, raw materials for intermediates of L-6-HTP derivative and L-6-HTP derivatives prepared by the present disclosure are low-cost and easy to purchase through commercial channels. The reactions involved have mild conditions, simple operations, high selectivity, and desirable operability of the separation and purification. The method shows a high product yield and exhibits a significant application value in the field of amino acid derivative synthesis.

The above descriptions are merely preferred embodiments of the present disclosure. It should be noted that a person of ordinary skill in the art may further make several improvements and modifications without departing from the principle of the present disclosure, but such improvements and modifications should be deemed as falling within the scope of the present disclosure.

What is claimed is:

1. A method for preparing an intermediate E of L-6-hydroxytryptophan (HTP), comprising the following steps:

subjecting a compound A6-0 to triisopropylsilyl (TIPS) protection to obtain an intermediate A of L-6-HTP;

subjecting the intermediate A of L-6-HTP to coupling to obtain an intermediate B of L-6-HTP, wherein the coupling is conducted in the presence of (1,5-cyclooctadiene)(methoxy)iridium(I) dimer, and 1,10-phenanthroline;

subjecting the intermediate B of L-6-HTP to carbon-boron bond oxidation to obtain the intermediate C of L-6-HTP, wherein the carbon-boron bond oxidation is conducted in the presence of sodium perborate tetrahydrate and potassium tert-butoxide (KTB), the carbon-boron bond oxidation comprises a first-stage reaction and a second-stage reaction in sequence, the first-stage reaction is conducted at a temperature of −10° C. to 10° C. for 1 h to 2 h; and the second-stage reaction is conducted at a temperature of 25° C. to 50° C. for 1 h to 24 h;

subjecting the intermediate C of L-6-HTP to hydroxyl-targeted benzyl protection to obtain the intermediate D of L-6-HTP; and subjecting the intermediate D of L-6-HTP derivative to TIPS protective group removal to obtain the intermediate E of L-6-HTP;

wherein the compound A6-0, the intermediate A of L-6-HTP, the intermediate B of L-6-HTP, the intermediate C of L-6-HTP, the intermediate D of L-6-HTP, and the intermediate E of L-6-HTP have structures shown in Formula 1, Formula 2, Formula 3, Formula 4, Formula 5, and Formula 6 respectively:

Formula 1

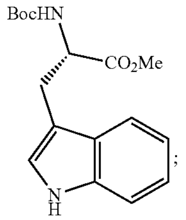

Formula 2

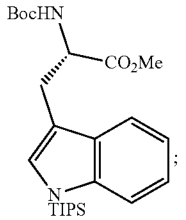

Formula 3

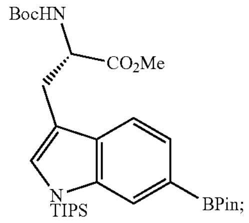

Formula 4

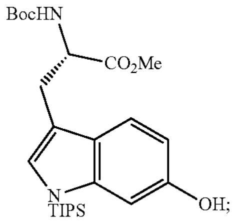

Formula 5

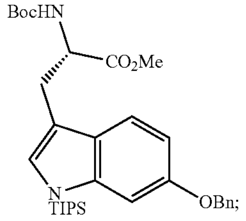

Formula 6

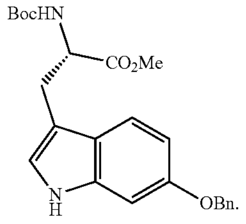

2. A method for preparing an intermediate F of L-6-HTP, comprising the following steps:

preparing the intermediate E of L-6-HTP by the method of claim 1; and subjecting the intermediate E of L-6-HTP to tert-butoxycarbonyl (Boc) protective group removal to obtain the intermediate F of L-6-HTP;

wherein the intermediate F of L-6-HTP has a structure shown in Formula 7:

Formula 7

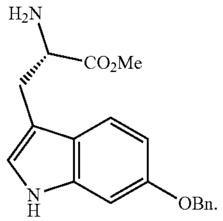

3. A method for preparing L-6-HTP, comprising the following steps:

preparing the intermediate F of L-6-HTP by the method of claim 2; and subjecting the intermediate F of L-6-HTP to methyl ester hydrolysis and amino-targeted 9-fluorenylmethoxycarbonyl (Fmoc) protection to obtain L-6-HTP;

wherein L-6-HTP has a structure shown in Formula 8:

Formula 8

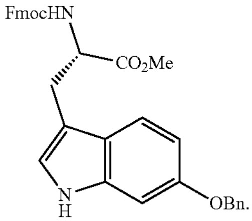

4. The method of claim 1, wherein a benzyl reagent for the hydroxyl-targeted benzyl protection comprises benzyl bromide, and the hydroxyl-targeted benzyl protection is conducted in the presence of potassium iodide and potassium carbonate.

5. The method of claim 1, wherein the TIPS protective group removal is conducted in the presence of tetrabutylammonium fluoride (TBAF).

6. The method of claim 2, wherein the Boc protective group removal is conducted in the presence of trifluoroacetic acid (TFA).

7. The method of claim 2, wherein a benzyl reagent for the hydroxyl-targeted benzyl protection comprises benzyl bromide, and the hydroxyl-targeted benzyl protection is conducted in the presence of potassium iodide and potassium carbonate.

8. The method of claim 3, wherein a benzyl reagent for the hydroxyl-targeted benzyl protection comprises benzyl bromide, and the hydroxyl-targeted benzyl protection is conducted in the presence of potassium iodide and potassium carbonate.

9. The method of claim 2, wherein the TIPS protective group removal is conducted in the presence of TBAF.

10. The method of claim 3, wherein the TIPS protective group removal is conducted in the presence of TBAF.

11. The method of claim 3, wherein the Boc protective group removal is conducted in the presence of TFA.

* * * * *